United States Patent [19]

Pianka

[11] 4,191,757

[45] * Mar. 4, 1980

[54] S-CHLOROMETHYL DIETHYLPHOSPHOROTHIOLOTHIONATE AS A SOIL INSECTICIDE

[75] Inventor: Max Pianka, Wembley Park, England

[73] Assignee: The Murphy Chemical Company Limited, St. Albans, England

[ * ] Notice: The portion of the term of this patent subsequent to Jul. 22, 1992, has been disclaimed.

[21] Appl. No.: 850,045

[22] Filed: Nov. 9, 1977

Related U.S. Application Data

[63] Continuation of Ser. No. 718,608, Aug. 30, 1976, abandoned, which is a continuation of Ser. No. 575,366, May 7, 1975, abandoned, which is a continuation of Ser. No. 401,692, Sep. 28, 1973, Pat. No. 3,896,219, which is a continuation of Ser. No. 169,875, Aug. 6, 1971, abandoned, which is a continuation of Ser. No. 842,291, May 13, 1969, abandoned.

[51] Int. Cl.$^2$ ............................................. A01N 9/36
[52] U.S. Cl. .................................................. 424/225
[58] Field of Search .......................................... 424/225

[56] References Cited

U.S. PATENT DOCUMENTS

| 2,931,755 | 4/1960 | Birum ................................. 424/225 |
| 3,439,092 | 4/1969 | Fearing et al. ...................... 424/225 |
| 3,896,219 | 7/1975 | Pianka ................................ 424/225 |

FOREIGN PATENT DOCUMENTS

| 817360 | 7/1959 | United Kingdom . |
| 1018314 | 1/1966 | United Kingdom . |

*Primary Examiner*—Leonard Schenkman
*Attorney, Agent, or Firm*—Bacon & Thomas

[57] ABSTRACT

The present invention provides a method for the control of insect pests and their larvae which are damaging to plants which comprises applying to soil containing said pests or larvae an effective amount of S-chloromethyl diethylphosphorothiolothionate.

9 Claims, No Drawings

5-CHLOROMETHYL DIETHYLPHOSPHOROTHIOLOTHIONATE AS A SOIL INSECTICIDE

CROSS REFERENCE TO RELATED APPLICATIONS

This is a continuation of application Ser. No. 718,608 filed Aug. 30, 1976 now abandoned, which is in turn a continuation of Ser. No. 575,366 filed May 7, 1975, now abandoned, which is in turn a continuation of Ser. No. 401,692 filed Sept. 28, 1973, now U.S. Pat. No. 3,896,219, which is a continuation of Ser. No. 169,875 filed Aug. 6, 1971, now abandoned, which in turn is a continuation of Ser. No. 842,291 filed May 13, 1969, now abandoned.

PRIOR ART

British Pat. No. 817,360 to Hoechst discloses S-chloromethyl dialkylphosphorothiolothionates and O-chloromethyl dialkylphosphorothionates as having unspecified insecticidal activity. The compounds are said to form valuable intermediate products for the production of other insecticides. The compound S-chloromethyl diethylphosphorothiolothionate is disclosed but no specific insecticidal properties of this compound are taught.

British Pat. No. 1,018,314 to Bayer teaches fungitoxic compositions containing as active ingredients thionothiolophosphoric acid esters of the general formula:

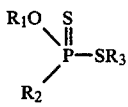

wherein $R_1$ is an alkyl radical containing up to 4 carbon atoms, $R_2$ is an alkoxy or alkylmercapto radical containing up to 4 carbon atoms and $R_3$ is an alkyl radical which may be substituted by a halogen atom or a hydroxyl, cyano or thiocyano group. No insecticidal activity for the compositions is taught; in fact it is suggested that insecticides be added to the composition. There is no exemplification of the application of any compound containing a chloromethyl group to soil.

U.S. Pat. No. 2,931,755 to Birum teaches that S-dichloromethyl O,O-dialkyl or O,O-bis(haloalkyl) phosphorothioates have contact insecticidal and fungicidal properties. There is no teaching of the application of the compounds to soil.

BACKGROUND TO THE INVENTION

A number of insects and their larvae in the soil are known to cause serious damage to agricultural and horticultural crops. These insects and their larvae include root flies such as the cabbage rootfly (*Hylemyia brassicae*) and wireworms (Agriotes, the larvae of the click beetle). For example, wireworms occur in practically all economically important crops e.g. wheat, sugar beet, carrots, potato and maize. Wireworms are a serious threat to world food production.

Insects and their larvae in the soil have been effectively controlled with halogenated hydrocarbons such as aldrin, dieldrin, heptachlor, D.D.T. and B.H.C. (benzene hexachloride). Unfortunately these compounds leave heavy and extremely persistent residues in the soil, amounting typically to 2 ppm from a single application of the compounds. The loss of these residues from the soil by leaching is very slow, and they are not fully broken down in the soil for many years. Furthermore, halogenated hydrocarbons tend to be concentrated and stored indefinitely in the lipid fraction of animal tissues, and species occupying the top positions of food chains, such as birds or prey and man, receive appreciable doses of these materials from normal agricultural use. Although previously considered to be valuable pesticides, the majority of these materials are now either banned completely in developed countries or restricted to a few specific uses.

Many alternatives have been found to the halogenated hydrocarbons for control of insects on plant foliage (topical application); for example, many organophosphorus derivatives have been found to be equally effective for this purpose. For use in the soil, on the contrary, it has been most difficult to find acceptable replacements for such compounds as aldrin and heptachlor.

Soil often has a pH quite widely different from neutrality; it also contains materials having catalytic activity and adsorptive properties, and it is infected with micro-organisms which have a wide range of biological capabilities. The combined effect of these factors is to degrade or inactivate the majority of insecticides applied to the soil quite rapidly, even if they are not leached out by railfall.

Most organophosphorus insecticides are either not active in the soil, or have an uneconomically short period of effectiveness. Some organophosphorus compounds which do show activity in the soil, such as phorate, are systemic and leave substantial crop residues. Wireworms have proved particularly resistant to most organophosphorus compounds, and without halogenated hydrocarbons control of this pest has often been barely adequate.

There is a long felt need for a compound which has potent and sustained insecticidal activity in the soil, but which does not contaminate the environment with objectionable toxic residues.

DESCRIPTION OF THE INVENTION

I have now discovered that effective control of insect pests on their larvae which are damaging to plants may be obtained by applying to soil containing said pests or larvae an effective amount of S-chloromethyl diethylphosphorothiolothionate.

The great effectiveness of this compound as a soil insecticide is most surprising, in view of its known chemical reactivity. It is, moreover, a poor contact insecticide compared with compounds commercially used for this purpose.

S-chloromethyl diethylphosphorothiolothionate lacks the undesirable persistency of the halogenated hydrocarbons, but nevertheless remains effective in the soil for far longer than its chemical reactivity would suggest. It has virtually ideal persistency characteristics as a soil insecticide, being capable of giving protection for the whole growing season. On the other hand the soil residues at the end of the season are negligible; the half-life in soil is about 20±6 days, depending on the nature of the soil and the climate. I have found that one application of the compound at the rate of 2–4 kg/ha gives control of soil living insects throughout the growing season, but at the end of the season the residue is of the order of 0.01 to 0.02 ppm. This compares with residues of the order of 2.0 ppm for halogenated hydrocarbons, i.e. 100–200 times the level for S-chloromethyl diethylphosphorothiolothionate.

S-Chloromethyl diethylphosphorothiolothionate is particularly effective against wireworms and, indeed, I believe it is more effective against this pest than any prior art compound, apart from certain halogenated hydrocarbons which leave noxious residues.

The toxicant is suitably applied to the soil at a rate of from 0.56–11.2 kg/ha. However good control of soil living insects is often obtained at rates of from 1.12–4.49 kg/ha.

The compound may conveniently be formulated as granules or powders containing an inert solid diluent such as fuller's earth impregnated with the toxicant. Such formulations may contain from 1 to 50% by weight of the toxicant, or more or less, and may be applied to the soil in any suitable manner. It will be understood that a more effective insecticidal action will generally result when the formulation is physically mixed with the topsoil, such as by harrowing.

The toxicant may be applied as a drench, that is a solution or dispersion of the toxicant in a non-phytotoxic solvent or liquid diluent, suitably water. Such drenches may be prepared by diluting with water a concentrate containing the toxicant, an emulsifying agent, and preferably an organic solvent such as naphtha. I have further found that the toxicant may be used as a seed dressing to control attack by insects and/or their larvae on the germinating seed. The seed may be treated by agitating it in contact with a composition containing the toxicant.

The seed dressing composition suitably includes a solid carrier or diluent e.g. china clay or talc. A surface active agent may be included, with or without additional solid carrier or diluent, when the dressing is to be applied in a moistened state.

A suitable colouring agent may conveniently be included, and also, if desired, a sticking agent, the latter to increase adherence of the dressing to the seed. Solid compositions may be used in encapsulation of the seed. The seed dressing composition may also be used as a liquid in solution or dispersion form in a non-phytotoxic liquid medium e.g. water or a non-phytotoxic organic solvent, to enable the seed to be impregnated or coated with the active ingredients. Such liquids may also contain colouring agents and/or stickers as described above.

The following examples of my invention are given for purposes of illustration only.

EXAMPLE 1

S-Chloromethyl diethylphosphorothiolothionate (hereinafter called "the toxicant") was tested for activity against cabbage rootfly larvae (*Hylemyia brassicae*). The method of testing was as follows:

270 g of sterilized soil (John Innes No. 1) is placed in the bowl of a rotary mixer, which is then activated, and the required amount of toxicant is added slowly in 30 ml of aqueous dispersion, giving a moisture content of 10%. The concentration which is recorded refers to the final concentration wt/wt in the soil, and therefore the 30 ml which is mixed with the soil is made up at ten times this concentration. The soil should be mixed for at least 30 seconds. After mixing, the soil is distributed into 3 plastic cups each containing a piece of peeled swede weighing about 50 g, so as to cover the uppermost part of the swede; any surplus soil is discarded. The cups are then covered with petri dish halves until infestation.

On the same day in which the soil is treated, 2–3 day old eggs of *Hylemyia brassicae* which have been floated off from the egg-laying medium are taken off in batches of 25's on to small pieces of black filterpaper, using a small paint-brush. When dry, each batch of 25 eggs is used to infest one cup. The eggs are sprinkled on the surface and the soil is disturbed slightly so that the eggs do not remain exposed on the surface. The cups are then covered with polyethylene squares, and placed in the constant temperature room (75° F.).

After about 10 days the cups are briefly examined and any with fungus growing over the surface are discarded (about 8% of the cups).

3 Weeks after treatment the cups are examined for pupae.

The total number of larvae and pupae are added together for each cup, and the percentage kill for each cup and the average percentage kill for each treatment are calculated. This is corrected for control mortality to obtain percentage control.

The results were as follows:

| Percentage control | | |
|---|---|---|
| 10 ppm | 3 ppm | 1 ppm |
| 100 | 100 | 68 |

EXAMPLE 2

The toxicant was tested for activity against wireworms (Agriotes, 3rd–5th instar larvae). The method of testing was as follows: 800 g of dry soil (John Innes No. 1 compost) which has been screened through a ¼" sieve is placed in the bowl of a rotary mixer; this is then activated and the required amount of toxicant is added slowly as a dispersion in 200 ml of water. The soil should be mixed for at least 30 seconds after emptying all the toxicant. It is then transferred to a 9"×4" polystyrene dish, and the amount of soil in the dish is re-weighed (counterbalancing the dish with a similar dish). The dish is labelled with the treatment, and weight of soil it contains, and is put aside for infestation.

Eight wireworms of suitable size are placed on the soil in each dish, and allowed to burrow into the soil for 30 minutes. Any which fail to do so are removed and replaced. Sixteen wheat seeds are then planted in two rows of eight, and the dishes are transferred to a constant-temperature cabinet at 15° C.

Three times per week (Mondays, Wednesdays and Fridays) the dishes are watered to their original weight. Once per week, any dead wireworms on the surface are removed and recorded.

Assessment is carried out 4 weeks after treatment. First the number of plants which have grown is counted; the number of these which have been damaged by wireworm is also recorded. The plants are removed, and the soil is tipped on to a shallow tray and is carefully sifted through for dead and living wireworms (this is made easier if the soil is dry, and so the last watering of the soil is best carried out at least three (but not more than five) days before assessment). Any missing wireworms are assumed to have died and disintegrated.

The percentage kill of each treatment is calculated, and this is corrected for any natural mortality.

The percentage of surviving plants and the percentage of those which are damaged are also recorded.

The results of the tests were as follows:

Percentage control 5 ppm (≅ 2.24 kg/ha)
91, 100, 100 (3 tests)

EXAMPLE 3

Example 2 was repeated with the difference that the toxicant was applied six weeks before infestation with wireworms. The results were as follows:

Percentage control 5 ppm (≅ 2.24 kg/ha)
86, 100 (2 tests)

EXAMPLE 4

The toxicant was tested under garden conditions for effectiveness against cabbage rootfly (*Hylemyia brassicae*). The compound was used as a drench.

25 g of the toxicant was mixed with 8 g of a mixture of anionic and non-ionic emulsifiers and made up to 100 ml with heavy naphtha. The concentrate was then diluted with water to the required concentration.

The 25% emulsifiable concentrate was diluted with water to give a concentration of 500 p.p.m. A quantity of 70 ml of this dilution was applied on the soil round the base of cabbage plants on the 30th June. The assessment of control of the cabbage root flies was carried out on the 26th July, by lifting the fifty-four plants and examining the roots by cutting them longitudinally and counting the larvae.

The following results were obtained:
Toxicant at 500 p.p.m. gave 0.10 larvae per root
Untreated gave 2.13 larvae per root
Thus a very high control of the infestation was obtained.

EXAMPLE 5

Example 4 was repeated, except that the toxicant was applied to the soil in the form of granules containing 5 wt% of the toxicant:

5 g of the toxicant was dissolved in 8 g of diacetone alcohol. The solution was mixed with 87 g of granules made of fuller's earth, measuring between 0.35 and 0.7 mm.

The granules were placed on the surface of the soil round each cabbage plant so as to give a concentration of 0.05 g of the toxicant per plant (1 g of granules). The treatment took place on the 8th June. The cabbage plants were lifted on the 31st August. The roots of the plants were then cut longitudinally and inspected for damage caused by the root fly.

The toxicant at 0.05 g per plant gave 25% damaged roots
Untreated gave 82% damaged roots The yield of the cabbage plants was assessed. There was a significant increase in the yield of plants treated with the toxicant.

EXAMPLE 6

The procedure of Examples 4 and 5 was repeated, using the toxicant both as a drench (as Example 4) and granules (as Example 5).

The following results were obtained:

| Formulation | Mean % Survival of plants | Mean weight of plants/replicate | Mean % of plants infested |
|---|---|---|---|
| drench | 100 | 203 | 0 |
| granules | 100 | 292 | 0 |
| control | 96 | 243 | 34.0 |

EXAMPLE 7

Example 6 was repeated with the difference that cauliflowers were used as the indicator plant. Assessment was made on the larvae of the second generation of flies. The results were as follows:

| Formulation | Mean % Survival of plants | Mean weight of plants/replicate | Mean % of plants infested |
|---|---|---|---|
| drench | 100 | 1150 | 0 |
| granules | 98 | 958 | 0 |
| control | 94 | 842 | 81.3 |

EXAMPLE 8

The toxicant was tested for activity against wireworms under garden conditions.

5% Granules of the toxicant prepared as in Example 5 were spread on soil and the soil was harrowed in order to bury the granules to a depth of about 3". Spring barley or wheat was then drilled and allowed to germinate (6–8 weeks).

The plants were inspected at random for damage; the damaged plants had yellowed and withered centre shoots. In addition the total number of plants in 3.05 m of row was recorded. This included healthy and damaged plants. Two tests were carried out, (I) using barley and (II) using wheat:

(I)

The toxicant at 2.24 kg/ha; 142 plants per 3.05 m row; 1.2% damaged plants; 954 ears per 7.3 m row
Untreated: 108 plants per 3.05 m row; 16.3% damaged plants; 602 ears per 7.3 m row

(II)

The toxidant at 2.27 kg/ha; 207 plants per 3.05 m row; 0.6% damaged plants
Untreated: 181 plants per 3.05 m row; 3.7% damaged plants There was a higher percentage of damaged plants in the untreated plants than in those treated with the toxicant. Therefore, in addition to a higher number of plants that were present per 3.05 m of row the crop had a vastly greater number of healthy plants in the case of the toxicant.

EXAMPLE 9

The toxicant was assessed for control of wireworms in sugar beet. The toxicant was made up as a 25% emulsifiable concentrate and diluted with water to give a concentration of 500 p.p.m. The diluted mixture was applied to the soil at the rate of 4.49 kg of toxicant per hectare.

The treated crop yielded 381 emerged plants, while the untreated control crop yielded 317 emerged plants.

EXAMPLE 10

Dressed seed according to the invention was prepared as follows. The toxicant (40 g) was adsorbed onto a highly adsorbent calcium silicate (15 g) and intimately mixed with china clay (45 g). The resulting mixture was then applied to seed using a conventional seed dressing apparatus.

I claim:

1. A method for the control of insect pests and their larvae in the soil which are damaging to plants which comprises applying to soil containing said pests or larvae an effective amount of S-chloromethyl diethylphosphorothiolothionate.

2. The method of claim 1 wherein from 0.56 kg/ha to 11.2 kg/ha of S-chloromethyl diethylphosphorothiolothionate is applied.

3. The method of claim 1 wherein from 1.12 to 4.49 kg/ha of S-chloromethyl diethylphosphorothiolothionate is applied.

4. The method of claim 1 wherein S-chloromethyl diethylphosphorothiolothionate is applied in the form of granules.

5. The method of claim 4, wherein the granules are physically mixed with the topsoil.

6. The method of claim 5, wherein the mixing is followed by planting seeds which germinate into said plants.

7. The method of claim 5, wherein the mixing is by harrowing.

8. The method of claim 4 wherein the granules are applied to the soil only in the vicinity of plants.

9. The method of claim 1, wherein S-chloromethyl diethylphosphorothiolothionate is applied to the soil as a drench.

* * * * *